United States Patent
Liang et al.

(10) Patent No.: US 12,319,656 B2
(45) Date of Patent: Jun. 3, 2025

(54) COMPOUND AS POTASSIUM CHANNEL REGULATOR AND PREPARATION AND USE THEREOF

(71) Applicant: Shanghai Zhimeng Biopharma, Inc., Shanghai (CN)

(72) Inventors: Bo Liang, Shanghai (CN); Gang Liu, Shanghai (CN); Huanming Chen, Shanghai (CN)

(73) Assignee: SHANGHAI ZHIMENG BIOPHARMA, INC., Shanghai (CN)

( * ) Notice: Subject to any disclaimer, the term of this patent is extended or adjusted under 35 U.S.C. 154(b) by 727 days.

(21) Appl. No.: 17/642,387

(22) PCT Filed: Dec. 20, 2021

(86) PCT No.: PCT/CN2021/139779
§ 371 (c)(1),
(2) Date: Mar. 11, 2022

(87) PCT Pub. No.: WO2022/174667
PCT Pub. Date: Aug. 25, 2022

(65) Prior Publication Data
US 2023/0212125 A1    Jul. 6, 2023

(30) Foreign Application Priority Data
Oct. 27, 2021 (CN) .......................... 2021112518651

(51) Int. Cl.
*C07D 217/04* (2006.01)

(52) U.S. Cl.
CPC .................................. *C07D 217/04* (2013.01)

(58) Field of Classification Search
CPC .................................................. C07D 217/04
See application file for complete search history.

(56) References Cited

U.S. PATENT DOCUMENTS

| | | | | |
|---|---|---|---|---|
| 2008/0139610 A1* | 6/2008 | Vernier | ............... | C07D 217/16 |
| | | | | 546/144 |
| 2011/0003850 A1* | 1/2011 | Vernier | ............... | A61P 25/04 |
| | | | | 546/144 |
| 2019/0343823 A1 | 11/2019 | Beatch | | |
| 2021/0147363 A1 | 5/2021 | Bichler et al. | | |
| 2021/0163429 A1 | 6/2021 | Chen et al. | | |
| 2022/0227721 A1 | 7/2022 | Chen et al. | | |
| 2023/0212125 A1 | 7/2023 | Liang et al. | | |

FOREIGN PATENT DOCUMENTS

| | | |
|---|---|---|
| CN | 101563085 A | 10/2009 |
| CN | 102869250 A | 1/2013 |
| CN | 110511220 A | 11/2019 |
| CN | 112384216 A | 2/2021 |
| CN | 113698345 A | 11/2021 |
| RU | 2218330 C2 | 12/2003 |
| WO | 1999037607 A1 | 7/1999 |
| WO | 2008024398 A2 | 2/2008 |
| WO | 2011094186 A1 | 8/2011 |
| WO | 2019217924 A1 | 11/2019 |
| WO | 2019223732 A1 | 11/2019 |

OTHER PUBLICATIONS

International Search Report issued Jun. 28, 2022 in International Application No. PCT/CN2021/139779.
Office Action issued Dec. 15, 2022 in RU Application No. 2022112447/04(026002).
Search Report issued Dec. 15, 2022 in RU Application No. 2022112447/04(026002).

* cited by examiner

*Primary Examiner* — Timothy R Rozof
(74) *Attorney, Agent, or Firm* — Panitch Schwarze Belisario & Nadel LLP

(57) ABSTRACT

A compound as a potassium channel regulator and preparation and use thereof are described. Specifically, the compound has the structure shown in formula A. A preparation method of the compound and its use as a potassium channel regulator in a medicament and a pharmaceutical composition are also described.

10 Claims, No Drawings

COMPOUND AS POTASSIUM CHANNEL REGULATOR AND PREPARATION AND USE THEREOF

CROSS-REFERENCE TO RELATED APPLICATIONS

This application is a Section 371 of International Application No. PCT/CN2021/139779, filed Dec. 20, 2021, which has not yet published, which claims priority under 35 U.S.C. § 119(b) to Chinese Application No. 2021112518651, filed Oct. 27, 2021, the disclosures of which are incorporated herein by reference in their entireties.

TECHNICAL FIELD

The invention relates to the field of biomedicine, in particular to compound as potassium channel regulator and preparation and use thereof.

BACKGROUND ART

Kv7 potassium channel is a type of voltage-dependent potassium ion channel with low threshold activation, slow activation and non-inactivation. The Kv7 potassium channel has five family members (Kv7.1-Kv7.5), all of which have similar topology, namely functional channel composed of four subunits, and each subunit contains six transmembrane fragments (S1-S6). Among which, S4 is a voltage sensing region which plays an important role in sensing membrane potential changes and controlling conformational changes: SS-S6 is the main components of the channel aperture region, and is the main combination and action region of potassium channel openers. Kv7.1 potassium channel is a non-neuronal pathway, which is distributed in the outer peripheral tissue, expressed in the heart to mediate myocardial Iks, and its mutation can lead to Long Q-T syndrome. Kv7.2-Kv7.5 potassium channel is the basis of neuronal M current, is widely distributed in the nervous system, and has a variety of physiological activity. Kv7.2 and Kv7.3 potassium channel gene mutation can lead to a variety of different epilepsy patterns, such as Benign familial neonatal convulsions (BFNC), which fully demonstrates the role of M current in regulating neuronal excitability. Kv7.4 potassium channel is highly expressed in the outer hair cells of the cochlea and brainstem auditory nucleus, and its mutation may cause hereditary deafness. Kv7.5 potassium channels are highly expressed in skeletal muscle and brain, and its mutation may cause retinopathy. Many diseases such as epilepsy, anxiety, deafness, etc., their common feature is high membrane excitability, and Kv7 potassium channels are the molecular basis of M current, which can be opened by sensing changes in membrane potential, so that the inhibitory potassium current is up-regulated, thus controlling membrane excitability so as to make the Kv7 potassium channels are of great significance in pain and mental illness represented by high nerve excitability.

Retigabine is a drug for treating epilepsy. It has been approved for marketing in the UK, Germany, and Denmark. Studies have confirmed that the role of Retigabine is related to the voltage-gated potassium ion channel (KCNQs), wherein its main mechanism of action is to regulate M-type potassium currents by acting on KCNQ2/3 channels.

Retigabine (RTG) is the first Kv7 potassium channel opener for assisting the treatment of adult partial-onset epilepsy marketed in 2011. In addition to anti-epilepsy, RTG can also be used to treat anxiety, neuralgia, neurodegenerative diseases, etc., RTG can effectively reduce or prevent seizures in a variety of epilepsy models. RTG shows effective anti-epileptic effects on both tonic seizures caused by the maximal electroshock seizure (MES) model and clonic seizures induced by PTZ. In addition, RTG can also prevent seizures caused by N-methyl-D-aspartate (NMDA), penicillin, picrotoxin, Kainic acid (KA), etc. The ignition model is suitable for screening a variety of antiepileptic drugs, and the effect of RTG on this model is stronger than other models. Due to the extensive effects of RTG on all Kv7 potassium channel members and other channels, its poor selectivity makes it potentially undesirable. A large number of literatures have reported that RTG has a high incidence of adverse events related to the central nervous system, which can lead to dizziness, fatigue, aphasia, speech disorders, balance disorders and other adverse reactions including kidney stones, urinary retention and other kidney and urinary system diseases, cardiac related diseases such as sudden cardiac arrest, transient non-sustained ventricular tachycardia, and can also cause retinal discoloration, blue/purple pigmentation on skin, nails and the like.

SUMMARY OF THE INVENTION

The object of the present invention is to provide a compound of formula A, a preparation method thereof, and its use as a potassium channel regulator.

In the first aspect of the present invention, it provides a compound shown in formula A or a pharmaceutically acceptable salt thereof,

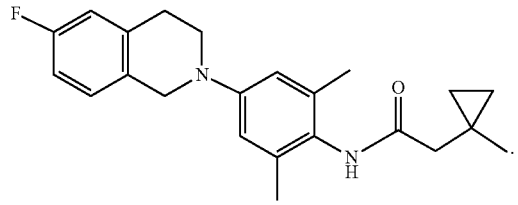

formula A

In the second aspect of the present invention, it provides a preparation method of the compound or the pharmaceutically acceptable salt according to the first aspect of the invention, comprising the steps:

1) reacting

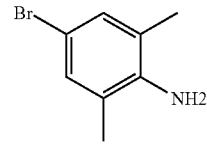

with

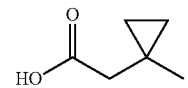

to obtain

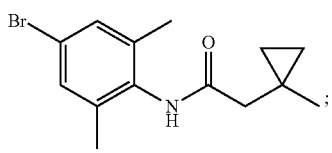 [SMILES: Cc1cc(Br)cc(C)c1NC(=O)CC1(C)CC1]

2) reacting

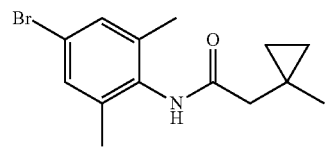 [SMILES: Cc1cc(Br)cc(C)c1NC(=O)CC1(C)CC1]

with

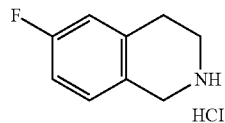

to obtain the compound of formula A.

In another preferred embodiment, in step 1), the molar ratio of

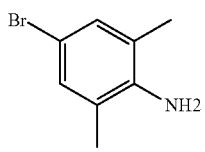

to

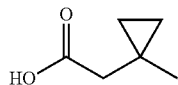

is 1:1-1.2, preferably 1:1.1.

In another preferred embodiment, in step 2), the molar ratio of

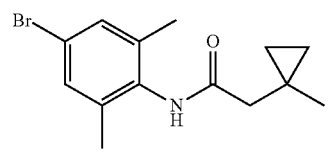

to

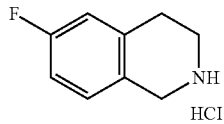

is 0.8-1.1, preferably 0.8-1.

In another preferred embodiment, the method comprises the following steps:

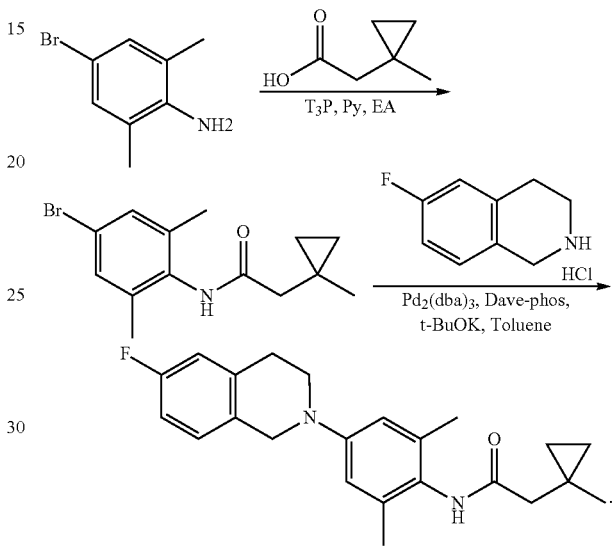

In the third aspect of the present invention, it provides a use of the compound or the pharmaceutically acceptable salt thereof according to the first aspect of the present invention for the preparation of a medicament for the treatment or prevention of a disease, disorder or condition affected by the regulation of potassium ion channels.

In the fourth aspect of the present invention, it provides a use of the compound or the pharmaceutically acceptable salt thereof according to the first aspect of the present invention for the preparation of a medicament for the treatment or prevention of a disease, disorder or condition affected by the regulation of potassium ion channel KCNQ2.

In the fifth aspect of the present invention, it provides a use of the compound or the pharmaceutically acceptable salt thereof according to the first aspect of the present invention for the preparation of a medicament for the treatment or prevention of a disease, disorder or condition affected by the regulation of potassium ion channel KCNQ2/3.

In the sixth aspect of the present invention, it provides a use of the compound or the pharmaceutically acceptable salt thereof according to the first aspect of the present invention for the preparation of a medicament for the treatment or prevention of a disease, disorder or condition affected by the regulation of potassium ion channel KCNQ3.

In the seventh aspect of the present invention, it provides a use of the compound or the pharmaceutically acceptable salt thereof according to the first aspect of the present invention for the preparation of a medicament for the treatment or prevention of a disease, disorder or condition affected by the regulation of potassium ion channel KCNQ3/5.

In the eighth aspect of the present invention, it provides a use of the compound or the pharmaceutically acceptable salt thereof according to the first aspect of the present invention for the preparation of a medicament for the treatment or prevention of a disease, disorder or condition affected by the regulation of potassium ion channel KCNQ4.

In another preferred embodiment, the disease, disorder or condition is a central nervous system disease.

In another preferred embodiment, the central nervous system disease is selected from the group consisting of epilepsy, convulsions, inflammatory pain, neuropathic pain, migraine, depression, anxiety disorder, stroke, Alzheimer's disease, neurodegenerative disease, cocaine abuse, nicotine withdrawal, alcohol withdrawal and tinnitus.

In the ninth aspect of the present invention, it provides a pharmaceutical composition comprising one or more pharmaceutically acceptable carriers and a therapeutically effective amount of one or more of the compounds or the pharmaceutically acceptable salt thereof according to the first aspect of the present invention.

In the tenth aspect of the present invention, it provides a method of preventing or treating a disease, disorder or condition affected by the regulation of potassium ion channels, comprising the step of administering to a subject in need thereof a therapeutically effective amount of the compound or the pharmaceutically acceptable salt thereof according to the first aspect of the present invention or the pharmaceutical composition of the ninth aspect of the present invention.

It should be understood that in the present invention, any of the technical features specifically described above and below (such as in the Examples) can be combined with each other so as to constitute new or preferred technical solutions, which will not redundantly be described one by one herein.

DETAILED DESCRIPTION OF THE INVENTION

After long-term and in-depth research, the present inventors unexpectedly prepared a compound represented by formula A with excellent potassium channel opening activity, maximum agonism rate of potassium ion channels, pharmacokinetics (such as cerebral blood ratio performance, etc.), in vivo efficacy and safety, and novel structure through structural optimization. On this basis, the inventors have completed the present invention.

Terms

In the present invention, unless specifically indicated, the terms used have the general meaning well known to those skilled in the art.

Compound

The invention provides a compound shown in formula A or a pharmaceutically acceptable salt thereof.

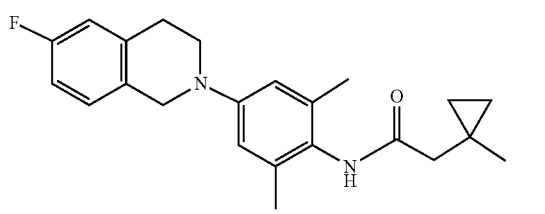 [SMILES: Cc1cc(N2CCc3cc(F)ccc3C2)cc(C)c1NCC(=O)CC(C)(C)C]

formula A

As used herein, the term "pharmaceutically acceptable salt" refers to a salt formed by a compound of the present invention with an acid or base suitable for use as a medicine. Pharmaceutically acceptable salts include inorganic salts and organic salts. A preferred class of salts is the salts of the compounds of the invention formed with acids. Suitable acids for forming salts include, but are not limited to inorganic acids such as hydrochloric acid, hydrobromic acid, hydrofluoric acid, sulfuric acid, nitric acid, phosphoric acid; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methylsulfonic acid, ethanesulfonic acid, p-toluenesulfonic acid, benzenesulfonic acid, naphthalenesulfonic acid; and amino acids such as proline, phenylalanine, aspartic acid and glutamic acid.

Another preferred class of salts are salts of the compounds of the invention formed with bases, such as alkali metal salts (such as sodium or potassium salts), alkaline earth metal salts (such as magnesium or calcium salts), ammonium salts (such as lower grades alkanol ammonium salts and other pharmaceutically acceptable amine salts), such as methylamine salt, ethylamine salt, propylamine salt, dimethylamine salt, trimethylamine salt, diethylamine salt, triethylamine salt, tert-butylamine salt, ethylenediamine salt, hydroxyethylamine salt, dihydroxyethylamine salt, trishydroxyethylamine salt, and an amine salt formed from morpholine, piperazine, and lysine, respectively.

Preparation Method

The preparation method of the compound of formula A according to the present invention is more specifically described below, but these specific methods do not constitute any limitation. The compounds of the present invention may also be conveniently prepared by optionally combining various synthetic methods described in the specification or known in the art, and such combinations are readily made by those skilled in the art to which the present invention pertains.

Typically, the preparation process of the compounds of the present invention is as follows, wherein the starting materials and reagents used are commercially available unless otherwise specified.

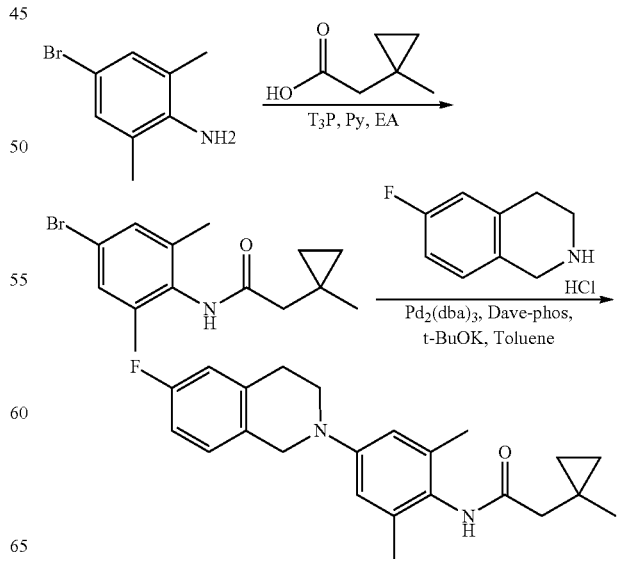

Pharmaceutical Composition and Method for Administration

The pharmaceutical composition of the present invention comprises a safe and effective amount of a compound of the present invention or a pharmacologically acceptable salt thereof, and a pharmacologically acceptable excipient or carrier. In which, "safe and effective amount" is meant that the amount of the compound is sufficient to significantly improve the condition without causing serious side effects. Generally, the pharmaceutical composition contains 1-2000 mg of the compound of the present invention/dose, more preferably, 5-1000 mg of the compound of the present invention/dose. Preferably, the "dose" is a capsule or tablet.

"Pharmaceutically acceptable carrier" means one or more compatible solid or liquid fillers or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soy bean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

The pharmaceutical composition is an injection, a capsule, a tablet, a pill, a powder, or a granule.

The administration mode of the compound or pharmaceutical composition of the present invention is not particularly limited, and representative administration modes include, but are not limited to, oral, intratumoral, rectal, parenteral (intravenous, intramuscular or subcutaneous) and topical administration.

Solid dosage forms for oral administration include capsules, tablets, pills, powders and granules. In these solid dosage forms, the active ingredient is mixed with at least one conventional inert excipient (or carrier), such as sodium citrate or dicalcium phosphate, or mixed with any of the following components: (a) fillers or compatibilizer, such as starch, lactose, sucrose, glucose, mannitol and silicic acid; (b) binders, such as hydroxymethyl cellulose, alginate, gelatin, polyvinylpyrrolidone, sucrose and arabic gum; (c) humectants, such as glycerol; (d) disintegrating agents such as agar, calcium carbonate, potato starch or tapioca starch, alginic acid, certain composite silicates, and sodium carbonate; (e) retarding solvents, such as wax, (f) absorption accelerators, such as quaternary ammonium compound; (g) wetting agents, such as cetyl alcohol and glyceryl monostearate; (h) adsorbents, such as kaolin; and (i) lubricants, such as talc, calcium stearate, magnesium stearate, solid polyethylene glycol, sodium dodecyl sulfate or mixture thereof. In capsules, tablets and pills, the dosage forms may also contain buffering agents.

Solid dosage forms such as tablets, dragees, capsules, pills and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric materials and waxy materials. If necessary, the active compound may also be in microencapsulated form with one or more of the above-mentioned excipients.

Liquid dosage forms for oral administration include pharmaceutically acceptable emulsions, solutions, suspensions, syrups or tinctures. In addition to the active compound, the liquid dosage form may contain inert diluents conventionally used in the art, such as water or other solvents, solubilizers and emulsifiers, such as ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances.

In addition to these inert diluents, the compositions may contain adjuvants such as wetting agents, emulsifying and suspending agents, sweetening agents, flavoring agents and spices.

In addition to the active compound, the suspension may contain suspending agent, such as ethoxylated isooctadecanol, polyoxyethylene sorbitol and dehydrated sorbitan ester, microcrystalline cellulose, aluminum methoxide and agar, or the mixture thereof etc.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Dosage forms for the compounds of the invention for topical administration include ointments, powders, patches, sprays and inhalants. The active ingredient is mixed under sterile conditions with a physiologically acceptable carrier and any preservatives, buffers, or propellants which may be required if necessary.

The compounds of the invention can be administered alone or in combination with other pharmaceutically acceptable compounds.

The treatment method of the present invention can be administered alone or in combination with other treatment means or therapeutic drugs.

When the pharmaceutical composition is used, a safe and effective amount of the compound of the present invention is administered to a mammal (such as a human) in need of treatment, wherein the dosage at the time of administration is the pharmaceutically effective dosage, for people having a body weight of 60 kg, the daily dose is usually 1~2000 mg, preferably 5~1000 mg. Of course, specific doses should also consider factors such as the administration route, the health of the patient, etc., which are within the skill of the skilled physician.

Compared with the prior art, the present invention has the following main advantages:
(1) the compound has better pharmacokinetic properties, such as better cerebral blood ratio, half-life, exposure, metabolic stability and other properties;
(2) The compound has better potassium ion channel opening activity, better maximum agonism rate of potassium ion channel, better ion channel selectivity, better in vivo efficacy and better safety;
(3) the compound is expected to be used for the treatment and/or prevention of diseases and conditions affected by the activity of potassium ion channels.

The present invention will be further illustrated below with reference to the specific examples. It should be understood that these examples are only to illustrate the invention but not to limit the scope of the invention. Experimental methods in which the specific conditions are not specified in the following examples are usually in accordance with conventional conditions such as the conditions described in Sambrook et al., Molecular Cloning: Laboratory Manual (New York: Cold Spring Harbor Laboratory Press, 1989), or in accordance with the conditions recommended by the manufacturer. Unless indicated otherwise, percentage and parts are calculated by weight.

Unless otherwise defined, all professional and scientific terminology used in the text have the same meanings as known to the skilled in the art. In addition, any methods and materials similar or equal with the recorded content can apply to the methods of the invention. The method of the preferred embodiment described herein and the material are only for demonstration purposes.

The experimental materials and reagents used in the following examples can be obtained from commercial sources unless otherwise specified.

Example 1 Preparation of Compound A

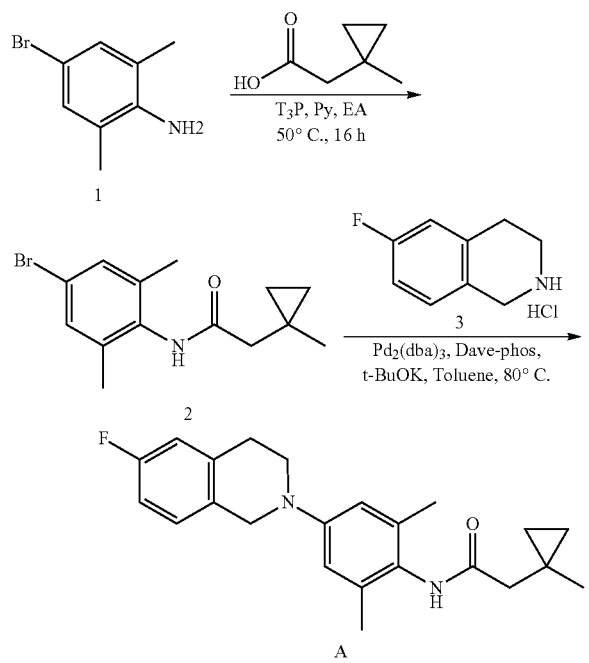

Step 1. Compound 2

Compound 1 (2.0 g, 10.0 mmol, 1.0 eq) was dissolved in ethyl acetate (100 mL), and 2-(1-methylcyclopropyl) acetic acid (cas: 71199-15-0, 1.26 g, 11.0 mmol, 1.1 eq), pyridine (7.9 g, 99.96 mmol, 10.0 eq) and $T_3P$ (50%, 31.8 g, 49.97 mmol, 5.0 eq) were added, the temperature was heated to 50° C., and the mixture was stirred for 16 hours. After cooling to 25° C., the mixture was diluted with water and extracted with ethyl acetate (3×100 mL). The combined organic phase was washed with saturated sodium chloride solution and dried over anhydrous sodium sulfate. The residue obtained after concentration was purified by silica gel column chromatography (petroleum ether/ethyl acetate=10/1) to obtain compound 2 (2.5 g, 84%) as a white solid.

LCMS: $[M+H]^+=296.0$

Step 2. Compound A

Compound 3 (224 mg, 0.61 mmol, 1.2 eq) was dissolved in toluene (5 mL), and compound 2 (150 mg, 0.51 mmol, 1.0 eq), potassium tert-butoxide (172 mg, 1.53 mmol, 3.0 eq), Dave-phos (40 mg, 0.10 mmol, 0.2 eq) and $Pd_2(dba)_3$ (47 mg, 0.051 mmol, 0.1 eq) were successively added, and the mixture was heated to 80° C. and stirred for 16 hours under the protection of nitrogen. The reaction solution was cooled to 25° C. and then diluted with ethyl acetate (30 mL), then washed with water and saturated sodium chloride solution in turn, the organic phase was dried over anhydrous sodium sulfate, and the residue obtained after concentration was purified by silica gel column chromatography (petroleum ether/ethyl acetate=2/1) to obtain compound A (52.3 mg, 28%).

LCMS: $[M+H]^+=367.2$ $^1$H NMR (400 MHZ, DMSO-$d_6$) δ 8.80 (s, 1H), 7.27-7.24 (m, 1H), 7.02-6.99 (m, 2H), 6.71 (s, 2H), 4.31 (s, 2H), 3.48 (t, J=6.0 Hz, 2H), 2.90 (t, J=6.0 Hz, 2H), 2.17 (s, 2H), 2.10 (d, 6H), 1.14 (s, 3H), 0.55-0.52 (m, 2H), 0.32-0.29 (m, 2H).

Example 2 Potassium Ion Channel Opener Agonism Rate Test (FDSS/μCELL Test)

1. Experimental Method:
1.1 Experimental Procedure

Cell preparation: CHO-KCNQ2 cells were cultured in a 175 cm$^2$ culture flask, and when the cell density grew to 60~80%, the culture medium was removed, washed with 7 mL PBS (Phosphate Buffered Saline) once, then 3 mL 0.25% Trypsin was added to digest. After the digestion was completed, 7 mL culture medium (90% DMEM/F12+10% FBS+ 500 μg/mL G418) was added to neutralize, centrifugated for 3 minutes at 800 rpm, the supernatant was aspirated, then 5 mL culture medium was added to resuspend, and then the cells were counted.

Cell plating: according to the results of cell counting, adjusted the density to 3×10$^4$ cells/well. After standing at room temperature for 30 minutes, placed in a 37° C. $CO_2$ incubator and incubated overnight for 16-18 hours. The cell density reached about 80%.

Fluorescent dye incubation: discarded the cell culture medium, 80 μL/well loading buffer was added, and incubated in the dark at room temperature for 60 minutes.

Compound incubation: discarded the loading buffer, 80 μL/well prepared compound solution was added, incubated in the dark at room temperature for 20 minutes.

Fluorescence data collection: FDSS/μCELL instrument was used for real-time fluorescence signal recording with excitation wavelength at 480 nm and emission wavelength at 540 nm, recorded 1 time per second, recorded for 10 seconds after baseline and started to add 20 μL/well stimulation buffer, and then continued to record until the end of 180 seconds.

1.2 Solution Preparation loading buffer: 10 mL/plate, the preparation method was as follows:

| Ingredient | Volume |
|---|---|
| PowerLoad™ concentrate, 100X (ingredient C) | 100 μL |
| FluxOR™ reagent, reconstituted in DMSO (step 1.2) | 10 μL |
| Deionized water | 8.8 mL |
| FluxOR™ test buffer, 10X (ingredient B) | 1 mL |
| Probenecid, reconstituted in deionized water (step 1.1) | 100 μL |
| Total volume | 10 mL |

Test buffer sample: 100 mL/plate, the preparation method was as follows:

| Ingredient | Volume |
|---|---|
| Deionized water | 8.9 mL |
| FluxOR ™ test buffer, 10X (ingredient B) | 1 mL |
| Probenecid, reconstituted in deionized water (step 1.1) | 100 µL |
| Total volume | 10 mL |

Stimulation buffer: 5 mL/plate, the preparation method was as follows:

| Ingredient | Volume $+K^+$ | Volume $-K^+$ |
|---|---|---|
| Deionized water | 2.5 mL | 3.5 mL |
| FluxOR ™ Chlorine-free buffer, 5X (ingredient E) | 1 mL | 1 mL |
| $K_2SO_4$ concentrate (125 mM $K_2SO_4$ concentrated solution, ingredient F) | 1 mL | / |
| $Tl_2SO_4$ concentrate (50 mM $Tl_2SO_4$ concentrate, ingredient G) | 0.5 mL | 0.5 mL |
| Total volumn | 5 mL | 5 mL |

The above buffer come from a commercially available kit named FluxOR potassium ion channel assay.

1.3 Compound Preparation 20 mM DMSO compound mother liquor was prepared, 10 µL of 20 mM compound mother liquor was took into 20 µL DMSO solution, serially diluted 3 times to 8 intermediate concentrations; then the middle concentration of the compound was took to the test buffer, 200 times dilution to get the final concentration to be tested, 80 µL was took and added to the test plate.

The highest test concentration was 100 µM, followed by 100, 33.33, 11.11, 3.70, 1.23, 0.41, 0.137, 0.045 µM, total 8 concentrations. Each concentration set 3 duplicate wells.

The content of DMSO in the final test concentration did not exceed 0.5%. This concentration of DMSO had no effect on the KCNQ2 potassium channel.

1.4 Data Analysis

Experimental data was analyzed by Excel 2007 and GraphPad Prism 5.0 software, and the ratio of 180 seconds was calculated to calculate the agonism effect. The agonism effect of the compound was calculated by the following formula:

Percentage of agonism =

$$\frac{\text{Fluorescence signal ratio with compound} - \text{Fluorescence signal ratio without compound}}{\text{Fluorescence signal ratio without compound}} \times 100\%$$

1.5 Quality Control

Environment: temperature ~ 25° C.

Reagent: FluxOR™ Detection Kit (Invitrogen, Cat #F0017)

The experimental data in the report must meet the following criteria: Z' Factor>0.5

2. Determined Results: See Table 1 for Details.

TABLE 1

| Compound | Maximum rate of agonism (%) |
|---|---|
| A | 43.06 |
| B | 9.67 |

References of the above test methods: ZhaobingGao et al., Journal of Biological Chemistry. 2010, 285 (36): 28322-28332.

Compound B is a compound having a structure of disclosed in patent WO2008024398 and WO2011094186. By comparing the maximum agonism rate of compound A and compound B, it can be seen that after the tert-butyl of compound B is changed into the maximum agonism rate of the compound to the potassium ion channel KCNQ2 is greatly increased (~ 4.5 times).

Example 3 Study of the Ability of Compounds to Pass Through the Blood-Brain Barrier 1) Research Purpose: In Order to Obtain the Situation of the Test Compound Passing Through the Blood-Brain Barrier 2) Experimental Content Nine healthy male ICR mice (body weight range 18-22 g) were taken and divided into 3 groups and 3 mice/group. After fasting overnight, the compound to be tested was given orally respectively. Blood was collected by cardiac puncture at the time points 1 h, 2 h and 4 h, and at least 0.5 mL of whole blood was collected to EDTA-K2 anticoagulant tube. Within half an hour, plasma was centrifuged (6000 revolutions, 8 minutes, 4° C.) and frozen at −20° C. for later use. At the same time, the brain tissue was collected, rinsed with normal saline, then sucked dry with absorbent paper, weighed, and frozen at −20° C. for later use.

Experimental results: According to the obtained blood drug concentration data, the non-compartmental model of WinNonlin® 7.0 software (Pharsight, USA) was used to calculate the pharmacokinetic parameters after administration.

TABLE 2 cerebral blood ratio at each time point after a single oral administration in male ICR mice

|  | 1 h cerebral blood ratio | 2 h cerebral blood ratio | 4 h cerebral blood ratio |
| --- | --- | --- | --- |
| Compound A | 4.47 | 3.31 | 4.24 |
| Compound B | 0.7 | 0.8 | 0.1 |

The cerebral blood ratio is very important for neurological drugs. The higher the cerebral blood ratio is, the stronger the ability of the compound to pass through the blood-brain barrier is. It can be seen from the comparison of the data in Table 2 that the cerebral blood ratio of compound A of the present invention is significantly better than that of compound B disclosed in patent WO2008024398 and WO2011094186 (more than 4 times).

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound shown in formula A or a pharmaceutically acceptable salt thereof,

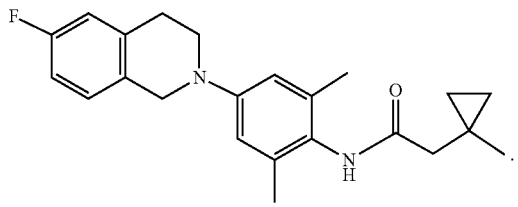

formula A

2. A method for preparing the compound or the pharmaceutically acceptable salt thereof of claim 1 comprising the steps:

1) Reacting

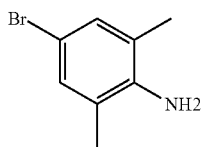

with

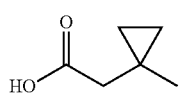

to obtain

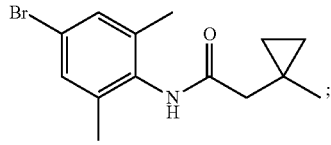 [SMILES: Cc1cc(Br)cc(C)c1NC(=O)CC1(C)CC1]

2) Reacting

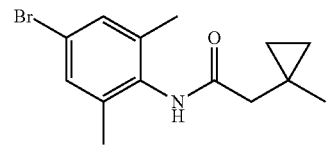 [SMILES: Cc1cc(Br)cc(C)c1NC(=O)CC1(C)CC1]

with

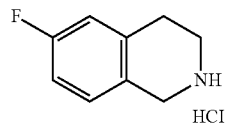

to obtain the compound of formula A.

3. A medicament for treating a disease, disorder or condition selected from the group consisting of epilepsy, convulsions, inflammatory pain, neuropathic pain, migraine, depression, stroke and neurodegenerative disease, wherein the medicament comprises the compound or the pharmaceutically acceptable salt thereof of claim 1.

4. The medicament of claim 3, wherein the disease, disorder or condition is selected from the group consisting of epilepsy and convulsions.

5. The medicament of claim 3, wherein the disease, disorder or condition is selected from the group consisting of inflammatory pain, neuropathic pain and migraine.

6. The medicament of claim 3, wherein the disease, disorder or condition is depression.

7. The medicament of claim 3, wherein the disease, disorder or condition is stroke.

8. The medicament of claim 3, wherein the disease, disorder or condition is a neurodegenerative disease.

9. A pharmaceutical composition comprising one or more pharmaceutically acceptable carriers and a therapeutically effective amount of one or more of the compounds or the pharmaceutically acceptable salts thereof of claim 1.

10. A method for treating a disease, disorder or condition selected from the group consisting of epilepsy, convulsions, inflammatory pain, neuropathic pain, migraine, depression, stroke and neurodegenerative disease, comprising administering the compound or the pharmaceutically acceptable salt thereof of claim 1 to a subject in need thereof.

* * * * *